(12) United States Patent
Fey

(10) Patent No.: US 9,291,112 B2
(45) Date of Patent: Mar. 22, 2016

(54) METHOD AND CONTROL UNIT FOR DETECTING A VOLTAGE OFFSET OF A VOLTAGE-LAMBDA CHARACTERISTIC CURVE

(71) Applicant: Michael Fey, Wiernsheim (DE)

(72) Inventor: Michael Fey, Wiernsheim (DE)

(73) Assignee: ROBERT BOSCH GMBH, Stuttgart (DE)

( * ) Notice: Subject to any disclaimer, the term of this patent is extended or adjusted under 35 U.S.C. 154(b) by 233 days.

(21) Appl. No.: 13/933,867

(22) Filed: Jul. 2, 2013

(65) Prior Publication Data

US 2014/0012486 A1 Jan. 9, 2014

(30) Foreign Application Priority Data

Jul. 5, 2012 (DE) .......................... 10 2012 211 687

(51) Int. Cl.
*F02D 41/00* (2006.01)
*F02D 41/14* (2006.01)
*G01N 27/417* (2006.01)

(52) U.S. Cl.
CPC ............ *F02D 41/00* (2013.01); *F02D 41/1454* (2013.01); *F02D 41/1474* (2013.01); *F02D 41/1475* (2013.01); *G01N 27/4175* (2013.01)

(58) Field of Classification Search
CPC . F02D 41/00; F02D 41/1454; F02D 41/1474; F02D 41/1475; G01N 27/4175
See application file for complete search history.

(56) References Cited

U.S. PATENT DOCUMENTS

| 5,036,819 A * | 8/1991 | Peter | F02D 41/1477 123/689 |
| 5,778,866 A * | 7/1998 | Uchikawa | F02D 41/008 123/682 |
| 2004/0244363 A1* | 12/2004 | Makki | F01N 11/007 60/285 |

FOREIGN PATENT DOCUMENTS

| DE | 38 27 978 | 5/1989 |
| DE | 198 60 463 | 7/2000 |
| DE | 10 2010 027 984 | 10/2011 |

\* cited by examiner

*Primary Examiner* — Stephen K Cronin
*Assistant Examiner* — Xiao Mo
(74) *Attorney, Agent, or Firm* — Kenyon & Kenyon LLP

(57) ABSTRACT

A method/control unit for detecting a voltage offset in a range of a voltage-lambda characteristic curve of a two-point lambda sensor in an engine exhaust gas duct as to a reference voltage-lambda characteristic curve of the two-point lambda sensor, which is part of a controlled system for adjusting an air-fuel mixture supplied to the engine, a characteristic curve deviation of voltage-lambda characteristic curve to the reference characteristic curve being corrected at $\lambda=1$, so that a change in the air-fuel mixture composition toward $\lambda=1$ occurs, starting from a value pair to be checked on the reference characteristic curve, with a lambda and a voltage to be checked, the actual value of lambda being inferred from the change in the mixture composition until reaching $\lambda=1$. The method/control unit permit determining and compensating a voltage offset of a two-point lambda sensor conditional upon aging or manufacturing tolerances.

14 Claims, 2 Drawing Sheets

METHOD AND CONTROL UNIT FOR DETECTING A VOLTAGE OFFSET OF A VOLTAGE-LAMBDA CHARACTERISTIC CURVE

RELATED APPLICATION INFORMATION

The present application claims priority to and the benefit of German patent application no. 10 2012 211 687.7, which was filed in Germany on Jul. 5, 2012, the disclosure of which is incorporated herein by reference.

FIELD OF THE INVENTION

The present invention relates to a method for detecting a voltage offset in at least one area of a voltage-lambda characteristic curve of a two-point lambda sensor situated in an exhaust gas duct of an internal combustion engine with respect to a reference voltage-lambda characteristic curve of the two-point lambda sensor, the two-point lambda sensor being part of a controlled system for adjusting an air-fuel mixture supplied to the internal combustion engine, a deviation in the voltage-lambda characteristic curve being corrected to the reference voltage-lambda characteristic curve at $\lambda=1$, the composition of the air-fuel mixture supplied to the internal combustion engine being changed toward $\lambda=1$, starting from a value pair on the reference voltage-lambda characteristic curve to be checked having a lambda value to be checked and a voltage to be checked, the actual value of lambda being inferred from the change in the composition of the air-fuel mixture until reaching $\lambda=1$.

The present invention also relates to a control unit for controlling an internal combustion engine and for determining the output voltage of a two-point lambda sensor in the exhaust gas duct of an internal combustion engine, the two-point lambda sensor being part of a controlled system for adjusting an air-fuel mixture supplied to the internal combustion engine.

BACKGROUND INFORMATION

For optimizing the pollutant emissions and the exhaust gas aftertreatment, lambda sensors are used in modern internal combustion engines to determine the composition of the exhaust gas and to control the internal combustion engine. Lambda sensors determine the oxygen content of the exhaust gas, which is used to regulate the fuel-air mixture supplied to the internal combustion engine and thus to regulate the exhaust gas lambda upstream from the catalytic converter. Air and fuel feeds to the internal combustion engine are regulated via a lambda control loop, to achieve an optimal composition of the exhaust gas for the exhaust gas aftertreatment by catalytic converters provided in the exhaust gas duct of the internal combustion engine. Gasoline engines are usually regulated to a lambda value of 1, i.e., a stoichiometric ratio of air to fuel. Pollutant emission by the internal combustion engine may be minimized in this way.

Various forms of lambda sensors are in use. In the case of a two-point lambda sensor, also known as a discrete-level sensor or Nernst sensor, the voltage-lambda characteristic curve has an abrupt drop at $\lambda=1$. It therefore essentially allows a differentiation between rich exhaust gas ($\lambda<1$) during operation of the internal combustion engine with excess fuel and lean exhaust gas ($\lambda>1$) during operation with excess air and permits regulation of the exhaust gas at a lambda value of 1.

A broad-band lambda sensor, also referred to as a continuous or linear lambda sensor, permits measurement of the lambda value in the exhaust gas in a wide range around $\lambda=1$. Thus, an internal combustion engine, for example, may also be regulated to a lean operation with excess air.

Steady lambda regulation upstream from the catalytic converter is also possible by linearization of the sensor characteristic curve, even using a less expensive two-point lambda sensor in a limited lambda range. The prerequisite for this is that there must be a definite correlation between lambda and the sensor voltage of the two-point lambda sensor. This correlation must be present over the entire lifetime of the two-point lambda sensor since otherwise the regulation accuracy will be inadequate, and inadmissibly high emissions may occur. This prerequisite is not met, due to manufacturing tolerances and aging effects of the two-point lambda sensor. Two-point lambda sensors upstream from the catalytic converter are therefore mostly used together with a two-point regulation. This has the disadvantage that the target lambda is adjustable only with precontrol but cannot be regulated for catalytic converter testing, for example, or for protection of components in operating modes for which a lean or rich air-fuel mixture is necessary.

Various methods are believed to be understood for calibrating the voltage-lambda characteristic curve of two-point lambda sensors.

German patent document DE 38 27 978 discusses how a voltage offset of the existing voltage-lambda characteristic curve may be determined and compensated with respect to a reference voltage-lambda characteristic curve of the two-point lambda sensor, which is constant over the entire lambda range, by balancing the sensor voltage during overrun fuel cutoff of the internal combustion engine. Furthermore, DE 10 2010 027 984 A1 describes a method for operating an exhaust gas system of an internal combustion engine in which at least one parameter of the exhaust gas flowing in an exhaust gas duct is detected by an exhaust gas sensor. It is provided that, during an operating state of the internal combustion engine in which there is no fuel injection or combustion, fresh air is supplied to the exhaust gas duct upstream from the exhaust gas sensor via a fresh air supply assigned to the exhaust gas system, and the exhaust gas sensor is adjusted during and/or after the fresh air supply.

However, sufficiently good compensation of the voltage offset is possible by this method only when it is equally pronounced, not only during overrun fuel cutoff with appropriate oxygen-containing exhaust gas but also in the entire lambda range. This may be the case if the voltage offset is due to a single cause. In most cases, however, there are multiple superimposed causes for a deviation in the voltage-lambda characteristic curve with respect to a reference voltage-lambda characteristic curve. These may be differently pronounced in different lambda ranges, whereby the voltage offset changes as a function of the lambda value of the exhaust gas. In particular the causes may be pronounced to different extents in the lean and rich lambda ranges. Such a voltage offset, which is a function of lambda, cannot be compensated adequately by an adjustment during overrun fuel cutoff. Another disadvantage of this method is that modern engine concepts have fewer and fewer overrun phases, which limits the possibility of such an overrun adjustment.

The publication DE 38 37 984 discusses a method in which a shift in the lambda-1 point of the voltage-lambda characteristic curve may be compensated via a control function by using a second lambda sensor installed downstream. A deviation in the voltage-lambda characteristic curve may thus be corrected at least to $\lambda=1$.

The publication DE 198 60 463 discusses a method for ascertaining the composition of the fuel-air mixture of an internal combustion motor during operation at a predefined setpoint interval from λ=1, in which method the actual interval from λ=1 is ascertained by temporarily adjusting the composition and analyzing the resulting response of a lambda sensor. It is thus provided that initially there is an abrupt adjustment by a defined value in the direction of λ=1, and next the lambda value is modified further at a defined rate of change until there is a response by the lambda sensor, and that the actual interval is ascertained from the value of the abrupt adjustment, the rate of change and the time until the lambda sensor responds.

This method permits determination of the actual lambda value which occurs in reality. If this actual lambda value differs from the lambda value expected on the basis of the measured output voltage of the lambda sensor, then an offset in the voltage-lambda characteristic curve may be inferred. The voltage-lambda characteristic curve may be corrected using the determined actual lambda value.

It is a disadvantage that dynamic effects in determining the actual interval of λ=1 are not taken into account. These dynamic effects may distort the result so much that it does not have the accuracy required for a steady lambda regulation using a two-point lambda sensor upstream from the catalytic converter, i.e., the accuracy required for detecting a characteristic curve offset.

SUMMARY OF THE INVENTION

An object of the present invention is to provide a simple and reliable method for detecting a voltage offset of a two-point lambda sensor during operation of the two-point lambda sensor to permit a steady lambda regulation using the two-point lambda sensor.

Another object of the present invention is to provide a corresponding control unit for carrying out the method.

The object of the present invention as it relates to the method is achieved by the fact that in a first method step, a lag time of the controlled system is determined; in a second method step, starting from the value pair to be checked, the composition of the air-fuel mixture is changed toward λ=1; the change in the composition is corrected using the lag time of the controlled system; the actual value of lambda in the value pair is determined from the corrected change in the composition of the air-fuel mixture, and a voltage offset of the voltage-lambda characteristic curve is detected from the deviation in the actual value of lambda from the value of lambda to be checked.

In particular, the exemplary embodiments and exemplary methods are to a method and control unit for detecting a voltage offset at least in a range of a voltage-lambda characteristic curve of a two-point lambda sensor situated in an exhaust gas duct of an internal combustion engine with respect to a reference voltage-lambda characteristic curve of the two-point lambda sensor, the two-point lambda sensor being part of a controlled system for adjusting an air-fuel mixture supplied to the internal combustion engine, a characteristic curve deviation of voltage-lambda characteristic curve to the reference voltage-lambda characteristic curve being corrected at λ=1, so that a change in the composition of the air-fuel mixture supplied to the internal combustion engine toward λ=1 takes place, starting from a value pair to be checked on the reference voltage-lambda characteristic curve, with a lambda to be checked and a voltage to be checked, and the actual value of lambda being inferred from the change in the composition of the air-fuel mixture until reaching λ=1. It is provided that a lag time of the controlled system is determined in a first method step, the change in the composition of the air-fuel mixture toward λ=1 taking place in a second method step, starting from the value pair to be checked, the change in the composition being corrected using the lag time of the controlled system, the actual value of lambda in the value pair being determined from the corrected change in the composition of the air-fuel mixture and a voltage offset of voltage-lambda characteristic curve being detected from a deviation in the actual value of lambda from the value of lambda to be checked. The method and the control unit permit the determination and compensation of a voltage offset of a two-point lambda sensor conditional upon aging or manufacturing tolerances.

This method permits detection of a deviation of the lambda value actually present from the lambda value expected and to be checked on the basis of the output signal of the two-point lambda sensor. Dynamic effects which result in a delay of the lambda signal during a lambda change are taken into account here. Voltage offsets due to tolerance and aging effects in the voltage-lambda characteristic curve with respect to the reference voltage-lambda characteristic curve of the two-point lambda sensor may thus be detected rapidly and accurately, while dynamic effects which would falsify the detection are compensated at the same time. The reference voltage-lambda characteristic curve indicates the correlation between the output voltage and the lambda value in the case of an intact two-point lambda sensor under standardized operating parameters. To correct the voltage offset, a new lambda value may be assigned to the voltage of the value pair to be checked.

The prerequisite for carrying out this method is that any existing shift in the lambda-1 point is compensated, as already described above.

The method takes into account the altered dynamics of the two-point lambda sensor with respect to the new condition. For this purpose, it may be provided that an abrupt change in the composition of the air-fuel mixture beyond λ=1 is carried out in the first method step, starting from the value pair to be checked, and the lag time is determined from the time difference between the abrupt change in the composition of the air-fuel mixture and reaching the output voltage of the two-point lambda sensor corresponding to λ=1. The point in time of the lambda jump is defined precisely by the abrupt change in the air-fuel mixture beyond λ=1. The time elapsing from the start of the lambda jump until the output signal of the two-point lambda sensor signals passage through λ=1 corresponds to the lag time of the controlled system and may be taken into account in correcting the change in the composition in the second method step. The abrupt change in the composition of the air-fuel mixture yields a chronologically precisely determined passage through λ=1, but other forms of the lambda change may also be used as an alternative.

According to a particular embodiment variant of the present invention, it may be provided that, in the second methods step, starting from the value pair to be checked, a change in the composition of the air-fuel mixture beyond λ=1 is carried out with a second ramp-type change in the composition of the air-fuel mixture at least in the range around λ=1, and that the actual lambda in the value pair to be checked is determined from the change in the composition of the air-fuel mixture until reaching the output voltage of the two-point lambda sensor corresponding to λ=1 minus the change in the composition of the air-fuel mixture during the lag time of the controlled system.

A lambda change from the value pair to be checked to λ=1 may be ascertained from the known change in the composition of the air-fuel mixture over time and the measured time until the output signal of the two-point lambda sensor signals λ=1. The measured time and thus the determined lambda change may be determined to be too large due to reduced dynamics of the two-point lambda sensor, for example. The measured time and thus the determined lambda change may be corrected by correction using the lag time of the controlled system determined in the first method step. The lambda change thus corrected then corresponds to the actual value of lambda in the value pair to be checked.

The composition of the air-fuel mixture may be changed using a constant ramp starting at the value pair to be checked. Alternatively, other forms of the lambda change may also be used. For example, first a defined abrupt change in the composition and a subsequent ramp-type change in the range of λ=1 may be provided. The abrupt change must not exceed the value of λ=1.

According to a particular embodiment variant of the present invention, it may be provided that a detected voltage offset in the voltage-lambda characteristic curve is corrected using the actual value of lambda and/or one or multiple causes for the voltage offset are inferred as a function of the detected voltage offset, and measures to prevent or reduce the causes are initiated. The correction may take place for the one value pair or for a predefined range of the voltage-lambda characteristic curve or the entire voltage-lambda characteristic curve.

The accuracy in determining the actual value of lambda may be increased by providing in the first method step a first ramp-type change in the composition of the air-fuel mixture to determine the lag time of the controlled system, and the slope of the second ramp-type change is adapted to the operating point of the internal combustion engine and/or in a second method step the slope of the second ramp-type change in the composition of the air-fuel mixture is adapted to the operating point of the internal combustion engine.

A further improvement in the accuracy of the method may be achieved by keeping the composition of the air-fuel mixture constant at the value pair to be checked for a stabilization period of the output signal of the two-point lambda sensor. The stabilization period may be predefined as a function of the operating point of the internal combustion engine.

A characteristic curve offset may be differently pronounced in the different ranges of the voltage-lambda characteristic curve. This is the case in particular when there are several causes for the characteristic curve offset. It may therefore be provided that the voltage offset is detected for various lambda ranges, in particular for a lean lambda range and for a rich lambda range. An adapted correction of the characteristic curve offset may then be provided for the various lambda ranges.

If it is provided that the value pairs to be checked are selected in such a way that a predefined setpoint lambda is maintained in the average over time, then a voltage offset may be detected without increased emissions by the internal combustion engine and corrected if necessary. For example, there may be a measurement with a lean exhaust gas composition at a setpoint lambda value of 1, following a measurement with a rich exhaust gas composition, so that the required lambda value of 1 is obtained in the average over time.

Errors in determining a voltage offset may be prevented by a plausibility check of the detection of the voltage offset by repeated measurements using the same value pair or by measurements using different value pairs. The accuracy in determining a voltage offset may be further improved by averaging and filtering the measuring results.

In the case of internal combustion engines operated temporarily with overrun fuel cutoff, it may be provided that a plausibility check takes place for the detection of the voltage offset during an overrun fuel cutoff of the internal combustion engine. This offers an additional and independent option for checking the ascertained voltage offset.

Detection and optional correction of a voltage offset may be carried out in various ranges of the voltage-lambda characteristic curve and thus starting from different value pairs to be checked. For this purpose, it may be provided that the value pair to be checked is adjusted in a targeted manner and/or that the voltage offset is detected with a value pair which occurs during operation of the internal combustion engine. In the latter case, system-induced active lambda changes, such as those carried out for catalytic converter tests, dynamic diagnoses of exhaust gas sensors or in phases with a two-point lambda regulation, for example, may be used for detection of a voltage offset without carrying out an active lambda change for this purpose.

The accuracy in detecting a voltage offset may be improved by carrying out the detection of the voltage offset during an operating point of the internal combustion engine which is constant for the duration of the detection. Carrying out the detection may therefore be linked to corresponding activation conditions.

A change in a voltage offset of a two-point lambda sensor usually takes place comparatively slowly. In order that there is a sufficiently well-corrected voltage-lambda characteristic curve already present when starting the internal combustion engine, it may be provided that before renewed detection of the voltage offset, the correction of the voltage offset from a preceding operating cycle of the internal combustion engine is used.

The object of the present invention relating to the control unit is achieved by configuring the control unit
- to adjust a value pair, which is to be checked, to a voltage-lambda characteristic curve by adjusting the composition of an air-fuel mixture,
- to predefine a change in the composition of the air-fuel mixture beyond λ=1 and to determine, from a lag time of the controlled system, the time lag in the jump response of the two-point lambda sensor,
- to predefine a ramp-type change in the composition of the air-fuel mixture, at least in the range of λ=1, starting from the value pair which is to be checked,
- to determine an actual value of lambda in the value pair to be checked, from the change in the composition of the air-fuel mixture between the value pair to be checked and reaching an output voltage of the two-point lambda sensor corresponding to λ=1 minus the change in the composition during the lag time of the controlled system, and
- to carry out a detection of a voltage offset of the voltage-lambda characteristic curve from a difference between the value to be checked and the actual value of lambda in the value pair to be checked.

The control unit thus makes it possible to carry out the method described here. The implementation may take place inexpensively through a corresponding software modification of the control unit.

The present invention is described in greater detail below on the basis of an exemplary embodiment illustrated in the figures.

DETAILED DESCRIPTION

Figure 1:
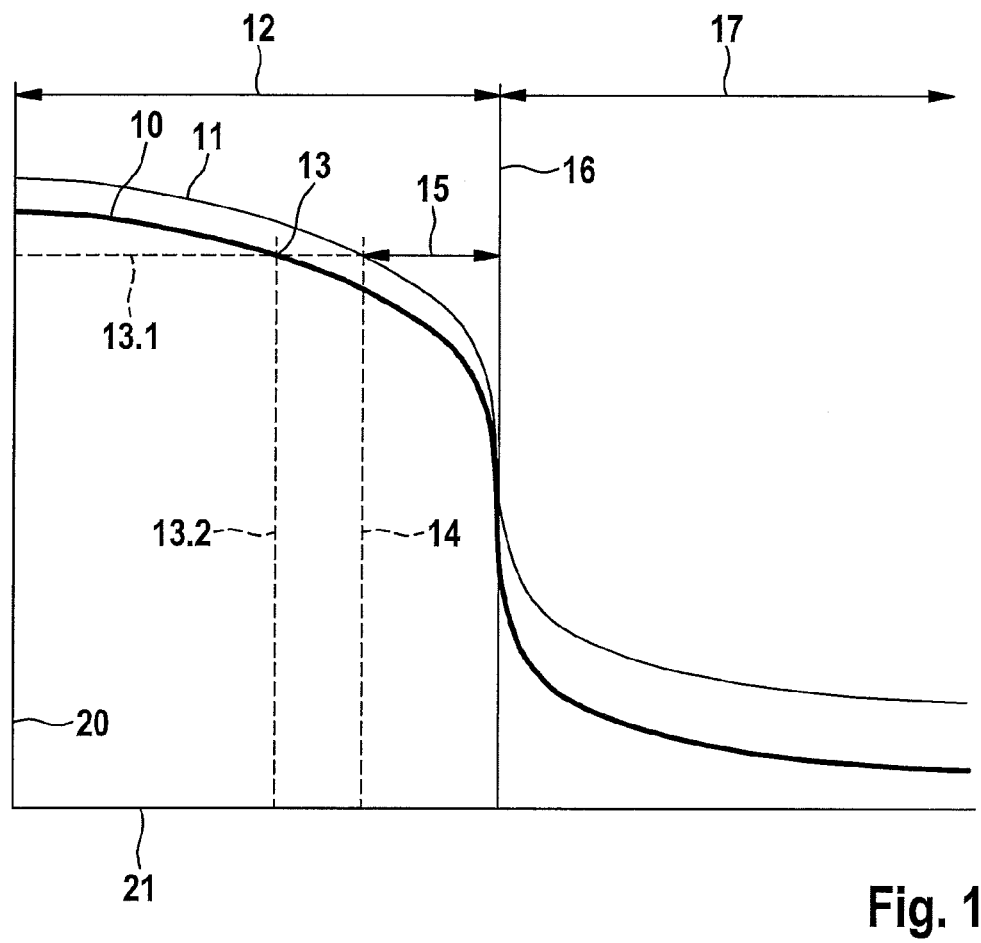
FIG. 1 shows a voltage-lambda characteristic curve of a two-point lambda sensor having a voltage offset with respect to a reference voltage-lambda characteristic curve.

FIG. 1 shows a voltage-lambda characteristic curve 11 of a two-point lambda sensor having a voltage offset with respect to a reference voltage-lambda characteristic curve 10. Characteristic curves 10, 11 are plotted here with respect to an axis for sensor voltage 20 and with respect to an axis for lambda 21.

The lambda range shown here is divided by a mark 16 at $\lambda=1$ into a rich lambda range 12, where $\lambda<1$, and a lean lambda range 17, where $\lambda>1$.

A value pair 13 to be checked is represented by a voltage 13.1 to be checked and a lambda 13.2 to be checked at the point of intersection of two broken lines on reference voltage-lambda characteristic curve 10. An actual value of lambda 14 is marked on voltage-lambda characteristic curve 11 for voltage 13.1 to be checked. A lambda change 15 due to a change in the air-fuel mixture supplied to the internal combustion engine and thus a lambda change until reaching $\lambda=1$ are represented by a double arrow.

Reference voltage-lambda characteristic curve 10 corresponds to the curve of the output signal of an intact unaged two-point lambda sensor in the exhaust gas duct of an internal combustion engine during a change in the exhaust gas composition. It has its maximum slope at $\lambda=1$. The abrupt change from a high output voltage to a low output voltage takes places in a comparatively small lambda window. Due to aging, due to manufacturing tolerances or due to changes in operating conditions of the two-point lambda sensor, its output voltage may shift by a voltage offset with respect to reference voltage-lambda characteristic curve 10.

In the present exemplary embodiment, voltage-lambda characteristic curve 11 has been shifted by a positive voltage offset with respect to reference voltage-lambda characteristic curve 10. The voltage offset here is more pronounced in lean lambda range 17 than in rich lambda range 12. Such a curve of the voltage offset is known, for example, for two-point lambda sensors which are operated too hot and have a constant voltage offset over the entire characteristic curve at the same time.

Use of a two-point lambda sensor for a steady lambda regulation upstream from the catalytic converter presupposes that a corresponding exhaust lambda may unambiguously be assigned to a certain sensor voltage. That is correct in the case of reference voltage-lambda characteristic curve 10. If there is a voltage offset of the actual voltage-lambda characteristic curve 11 with respect to the reference voltage-lambda characteristic curve 10, this assignment is no longer applicable. In the case of a voltage offset toward higher sensor voltages, as shown in the exemplary embodiment depicted here, a predefined sensor voltage is established at a lambda that is too lean. In the case of a voltage offset toward lower sensor voltages, the same sensor voltage is established at a lambda that is too rich. A lambda regulation using a voltage-lambda characteristic curve 11 shifted by a positive voltage offset thus results in a leaner exhaust gas, whereas a voltage-lambda characteristic curve shifted by a negative voltage offset results in a rich exhaust gas, which in turn results in increased pollutant emissions by the internal combustion engine.

A voltage offset of voltage-lambda characteristic curve 11 may be detected by determining the actual value of lambda 14 at a voltage 13.1 to be checked of the two-point lambda sensor from a change in the air-fuel ratio supplied to the internal combustion engine, the change being carried out in a targeted manner until reaching $\lambda=1$ and by comparing it with lambda 13.2 to be checked. If a deviation is found, the actual value of lambda 14 may be assigned to voltage 13.1 to be checked and voltage-lambda characteristic curve 11 may be corrected accordingly. Voltage-lambda characteristic curve 11 may be corrected in a larger range, for example, in a rich lambda range 12. It is provided according to the present invention that possible dynamic effects of the two-point lambda sensor are taken into account in determining the actual value of lambda 14. The dynamic effects may be due to an aging-induced dynamic loss of the two-point lambda sensor, and its effect is to be ascertained before determining the actual value of lambda 14.

Alternatively or in addition to the correction of voltage-lambda characteristic curve 11, the cause of the voltage offset may be inferred from the voltage offset and/or from the curve of the voltage offset, and measures may be taken to prevent or reduce the influence of these causes. In the exemplary embodiment shown here, for example, the constant voltage offset may be initially corrected, for example, and subsequently the temperature of the two-point lambda sensor may be reduced to adapt voltage-lambda characteristic curve 11 to reference voltage-lambda characteristic curve 10.

The prerequisite for detecting a voltage offset as described here is that any existing shift in the lambda-1 point as well as a constant offset of voltage-lambda characteristic curve 11 has already been compensated by known methods, so that voltage-lambda characteristic curve 11 corresponds to the reference voltage-lambda characteristic curve 10 at the lambda-1 point.

The causes may be corrected and compensated separately in different ranges of voltage-lambda characteristic curve 11. In the case of complete compensation, voltage-lambda characteristic curve 11 is congruent with reference voltage characteristic curve 10. It is thus possible to obtain an unambiguous correlation between the sensor voltage and lambda, even with an aged two-point lambda sensor. Steady lambda regulation upstream from the catalytic converter may thus be carried out in a limited lambda range even using an inexpensive two-point lambda sensor in comparison with a broad-band lambda sensor.

Figure 2:
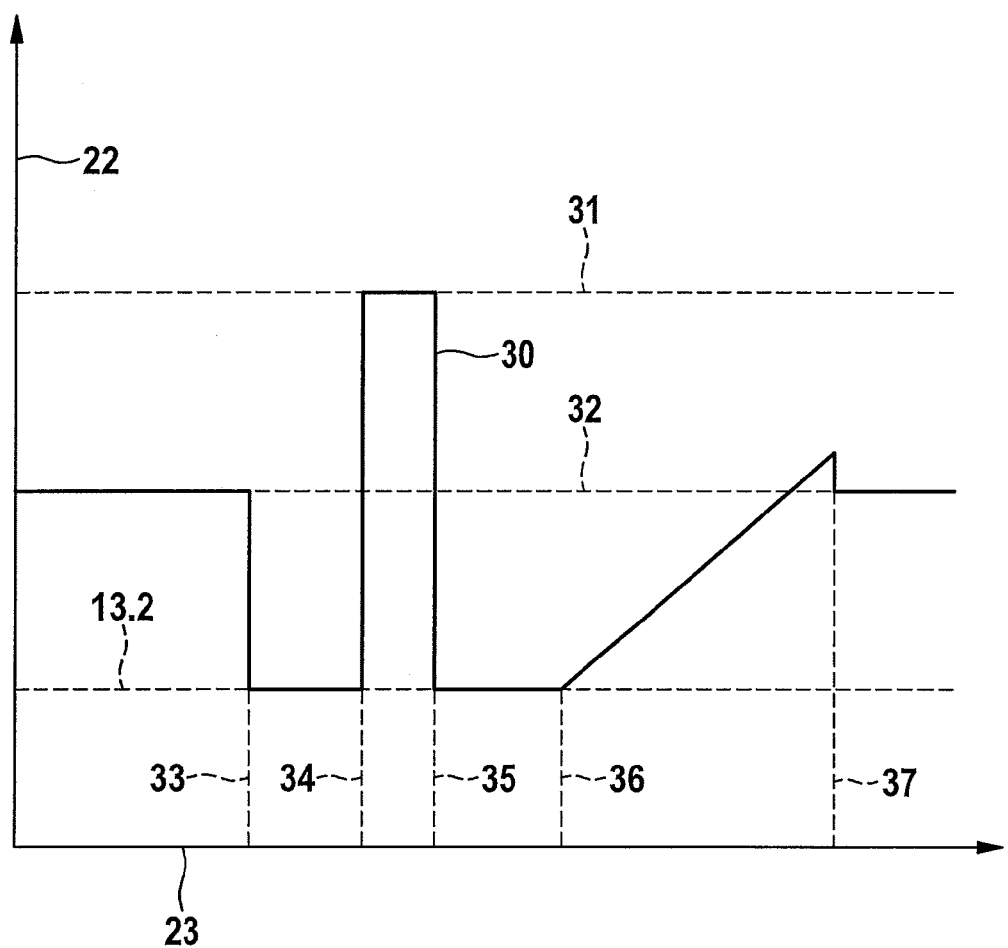
FIG. 2 shows a lambda curve over time for detecting a voltage offset.

FIG. 2 shows in one exemplary embodiment a lambda curve 30 over time for detecting a voltage offset in the case of a two-point lambda sensor having a delayed response. Lambda curve 30 is plotted with respect to an axis for setpoint lambda 22 and a time axis 23. A lean lambda 31, a setpoint $\lambda=1$ 32 and lambda 13.2, which is shown in FIG. 1 and is to be checked, are marked by dotted lines with respect to the axis for setpoint lambda 22. Accordingly, a first point in time t1 33, a second point in time t2 34, a third point in time t3 35, a fourth point in time t4 36 and a fifth point in time t5 37 are indicated with respect to time axis 23.

Lambda 13.2, which is to be checked, belongs to a value pair 13, which is to be checked and is shown in FIG. 1 on reference voltage-lambda characteristic curve 10 of the two-point lambda sensor. In the exemplary embodiment shown here, lambda 13.2 to be checked has a value of 0.95.

The two-point lambda sensor is part of a controlled system for adjusting an air-fuel mixture supplied to the internal combustion engine. In a first method step for determining a lag time of the controlled system, the air-fuel mixture supplied to the internal combustion engine is altered at first point in time t1 33 in such a way that lambda 13.2, which is to be checked, is present according to reference voltage-lambda characteristic curve 10. After a predefined stabilization time for the sensor voltage, an abrupt lambda change beyond λ=1 to a lean lambda 31 of 1.05, for example, takes place at second point in time t2 34.

The abrupt lambda change from a rich lambda to lean lambda 31 causes an abrupt change in the sensor voltage at λ=1. This abrupt change in the sensor voltage occurs with a lag due to dynamic effects. The lag time between the impression of the abrupt lambda change and the jump in the sensor voltage at λ=1 is measured.

After the lag time of the controlled system has been determined, in a second method step at third point in time t3 35, lambda 13.2, which is to be checked, is again adjusted and kept constant for a stabilization time. Output voltage U(t4) of the two-point lambda sensor is measured at fourth point in time t4 36. Starting from lambda 13.2 to be checked, a ramp-type lambda change in the direction of lean lambda values takes place from fourth point in time t4 36. The slope of the ramp-type lambda change may be constant and is adapted to the operating point of the internal combustion engine.

The ramp-type lambda change from a rich lambda to a lean lambda also causes an abrupt change in the sensor voltage at λ=1. This abrupt change also takes place with a time lag at a fifth point in time t5 37. The lag time corresponds to the lag time measured in the first method step.

Immediately after the abrupt change in the sensor voltage at λ=1, the ramp-type lambda change may be terminated and a desired setpoint lambda may be set.

The actual value of lambda 14 at fourth point in time t4 immediately at the start of the ramp-type lambda change corresponds to the lambda change which was required until the sensor voltage has made the abrupt change to fifth point in time t5 at λ=1 minus the lambda change which occurred during the lag time measured in the first method step.

The deviation between the actual value of lambda 14 ascertained at fourth point in time t4 36 and lambda 13.2 to be checked, which is expected at output voltage U(t4) according to reference voltage-lambda characteristic curve 10, corresponds to the characteristic curve offset at this point of voltage-lambda characteristic curve 11.

Due to the fact that the influence of dynamic effects is ascertained immediately before the actual value of lambda 14 is measured, this lambda measurement is much more accurate in comparison with those of previous methods. The characteristic curve offset thereby ascertained may then be used for adapting the sensor characteristic curve or for compensating causes resulting in the offset.

The abrupt or ramp-type lambda changes described in the first method step and in the second method step are particularly advantageous for rapid and accurate detection of a characteristic curve offset. In principle, however, other types of lambda changes are also conceivable, allowing the influence of dynamic effects to be ascertained and allowing the actual lambda values to be ascertained at a certain sensor voltage.

The stabilization times as well as the slope of the ramp may be adapted to the corresponding operating point of the internal combustion engine to increase the detection accuracy.

If a characteristic curve offset is pronounced differently in different areas of voltage-lambda characteristic curve 11, as shown in the exemplary embodiment in FIG. 1, the method may be accordingly applied for several value pairs to be checked and the voltage offset may be ascertained section by section.

A plausibility check may be carried out on the ascertained voltage offset by repeating the measurement at the same point or at other points on voltage-lambda characteristic curve 11. Detection results may be improved by averaging or filtering of the measuring result.

A plausibility check may be carried out on the ascertained characteristic curve offset by carrying out a measurement during overrun compensation in the case of internal combustion engines which allow overrun compensation.

It is advantageous to save a characteristic curve offset ascertained in a previous operating cycle of the internal combustion engine and to transfer it to the next operating cycle. It may be assumed that a characteristic curve offset will change only slowly. Thereby, a corrected voltage-lambda characteristic curve 11 of the two-point lambda sensor is immediately present in the next operating cycle.

The lambda changes described here may be activated for detection of a voltage offset. Alternatively or in addition, it may be provided that system-related active lambda changes such as those provided for catalytic converter testing, for diagnoses of exhaust gas sensors or in phases of a two-point lambda regulation, for example, may be used for detection.

Following a measurement in rich lambda range 12 of voltage-lambda characteristic curve 11, a corresponding measurement may take place in lean lambda range 17 and vice versa. The setpoint lambda is therefore retained in the average over time and the method may be carried out in an emission-neutral manner.

What is claimed is:

1. A method for detecting a voltage offset in a range of a voltage-lambda characteristic curve of a two-point lambda sensor situated in an exhaust gas duct of an internal combustion engine with respect to a reference voltage lambda characteristic curve of the two-point lambda sensor, the two-point lambda sensor being part of a controlled system for adjusting an air-fuel mixture supplied to the internal combustion engine, the method comprising:
   for at least one value pair in a set of value pairs:
      determining a lag time of the controlled system;
      checking a reference lambda value from the reference voltage-lambda characteristic curve;
      changing a composition of the air-fuel mixture to λ=1;
      correcting the changed composition based on the determined lag time;
      determining an actual value of lambda from the changed composition of the air-fuel mixture; and
      detecting a voltage offset of the voltage-lambda characteristic curve based on a deviation in the determined actual value of lambda from the checked reference value of lambda;
   wherein the at least one value pair includes a set of coordinates on the reference voltage-lambda characteristic curve having the reference lambda value and a reference voltage value, and wherein the set of value pairs begins at an endpoint of a range of the voltage-lambda characteristic curve and ends at λ=1.

2. The method of claim 1, further comprising:
   abruptly changing the composition of the air-fuel mixture beyond λ=1; and
   determining the lag time from a difference over time between a time of the abrupt change and a time at which an output voltage of the two-point lambda sensor corresponding to λ=1 is reached.

3. The method of claim 1, further comprising:
   changing the composition of the air-fuel mixture beyond λ=1 using a first ramp-type change at least in the range around λ=1, starting from the at least one value pair,
   wherein the actual lambda is determined from a change in the composition of the air-fuel mixture until reaching an output voltage of the two-point lambda sensor corresponding to λ=1 minus a change in the composition of the air-fuel mixture during the determined lag time of the controlled system.

4. The method of claim 1, wherein at least one of: (i) the detected voltage offset of the voltage-lambda characteristic curve is corrected using the determined actual value of lambda and (ii) one or multiple causes of the voltage offset are inferred as a function of the detected voltage offset and measures are taken to prevent or reduce the inferred causes.

5. The method of claim 3, wherein:
the lag time of the controlled system is determined by providing a second ramp-type change in the composition of the air-fuel mixture, and
a slope of the first ramp-type change is at least one of: adapted to an operating point of the internal combustion engine and adapted, during the changing of the composition of the air-fuel mixture to λ=1, to the operating point of the internal combustion engine.

6. The method of claim 1, wherein the composition of the air-fuel mixture is kept constant at the reference lambda value of the at least one value pair for a stabilization period of time.

7. The method of claim 1, wherein the voltage offset is detected for various lambda ranges, including for a rich lambda range and a lean lambda range.

8. The method of claim 1, wherein the at least one value pair is selected so that a predefined setpoint lambda is maintained as an average lambda value over time.

9. The method of claim 1, wherein a plausibility check is carried out on the detected voltage offset by repeated measurements with the at least one value pair or by measurements using different value pairs selected from the set of value of pairs.

10. The method of claim 1, wherein a plausibility check is carried out on the detected voltage offset during an overrun fuel cutoff of the internal combustion engine.

11. The method of claim 1, wherein at least one of: the composition of the air-fuel fixture is adjusted in a targeted manner from the value pair to be checked and the voltage offset is detected for a value pair from the set of value pairs, which occurs during operation of the internal combustion engine.

12. The method of claim 1, wherein the voltage offset is detected during an operating point of the internal combustion engine which is constant for the duration of the detection.

13. The method of claim 1, wherein the correction of the voltage offset from a preceding operating cycle of the internal combustion engine is used before a renewed detection of the voltage offset.

14. A control unit for controlling an internal combustion engine and for determining an output voltage of a two-point lambda sensor in an exhaust gas duct of the internal combustion engine, the two-point lambda sensor being part of a controlled system for adjusting an air-fuel mixture supplied to the internal combustion engine, the control unit comprising:
a control arrangement configured to perform the following for at least one value pair in a set of value pairs available from a reference voltage-lambda characteristic curve:
adjusting a composition of the air-fuel mixture from a first lambda value to a reference lambda value of the at least one value pair;
readjusting the composition from the reference lambda value to a predefined value beyond λ=1;
determining a lag time of the controlled system in a step response of the two-point lambda sensor from a first time at which the air-fuel mixture is at the reference lambda value to a second time at which the air-fuel mixture is at the predefined value;
subsequent to the composition returning to the reference lambda value, changing the composition of the air-fuel mixture according to a predefined ramp-type change from the reference lambda value to a value at least in the range of λ=1;
determining an actual value of lambda for the two point lambda sensor that corresponds to the at least one value pair based on the change in the composition of the air-fuel mixture between the at least one value pair and an output voltage of the two point lambda sensor corresponding to λ=1 minus a change in the composition during the determined lag time of the controlled system; and
detecting a voltage offset of a voltage-lambda characteristic curve of the two-point lambda sensor based on a difference between the reference lambda value and the determined actual value of lambda;
wherein the at least one value pair includes a set of coordinates on the reference voltage-lambda characteristic curve having the reference lambda value and a reference voltage value, and wherein the set of value pairs begins at an endpoint of the range of the voltage-lambda characteristic curve and ends at λ=1.

\* \* \* \* \*